(12) United States Patent
Tranzeat et al.

(10) Patent No.: US 8,882,998 B2
(45) Date of Patent: Nov. 11, 2014

(54) DEVICE FOR DISPENSING A VOLATILE SUBSTANCE

(75) Inventors: Lyse Tranzeat, West Drayton (GB); Guy Edmund Robinson, London (GB); Nicholas O'Leary, Pennington, NJ (US)

(73) Assignee: Firmenich SA, Geneva (CH)

( * ) Notice: Subject to any disclaimer, the term of this patent is extended or adjusted under 35 U.S.C. 154(b) by 731 days.

(21) Appl. No.: 13/139,571

(22) PCT Filed: Dec. 14, 2009

(86) PCT No.: PCT/IB2009/055743
§ 371 (c)(1),
(2), (4) Date: Jul. 28, 2011

(87) PCT Pub. No.: WO2010/070576
PCT Pub. Date: Jun. 24, 2010

(65) Prior Publication Data
US 2011/0290908 A1    Dec. 1, 2011

(30) Foreign Application Priority Data

Dec. 15, 2008    (WO) .................. PCT/IB2008/055300

(51) Int. Cl.
| | |
|---|---|
| *A61L 9/12* | (2006.01) |
| *A61L 9/04* | (2006.01) |
| *A01M 1/20* | (2006.01) |
| *A61L 2/18* | (2006.01) |

(52) U.S. Cl.
CPC ............... *A61L 9/04* (2013.01); *A61L 2209/15* (2013.01); *A61L 2/18* (2013.01); *A01M 1/2033* (2013.01); *A01M 1/2044* (2013.01); *A61L 9/127* (2013.01)
USPC .................. 210/87; 239/34; 239/44; 239/45; 239/50; 239/51.5; 239/57; 239/58; 239/59; 422/5; 422/123; 422/124

(58) Field of Classification Search
CPC ............. A61L 2/18; A61L 9/04; A61L 9/042; A61L 9/044; A61L 9/046; A61L 9/00; A61L 9/127; A61L 9/12; A61L 9/122; A61L 9/125; A61L 2209/15; A01M 1/2044; A01M 1/2033
USPC .......... 239/6, 45, 44, 47, 50, 34, 51.5, 57, 58, 239/59; 210/87; 422/5, 123, 124
See application file for complete search history.

(56) References Cited

U.S. PATENT DOCUMENTS

| | | | |
|---|---|---|---|
| 6,103,201 A | 8/2000 | Green | 422/124 |
| 6,764,656 B1 | 7/2004 | Matulevich | 422/124 |

(Continued)

FOREIGN PATENT DOCUMENTS

| | | |
|---|---|---|
| WO | WO 2005/030277 A1 | 4/2005 |
| WO | WO 2006/061803 A1 | 6/2006 |
| WO | WO 2007/036062 A2 | 4/2007 |

OTHER PUBLICATIONS

"Lever", Levers: Simple Machines, 2000.*

(Continued)

*Primary Examiner* — Allison Fitzsimmons
(74) *Attorney, Agent, or Firm* — Winston & Strawn LLP

(57) ABSTRACT

The present invention relates to the field of perfumery and more precisely it concerns a device, and the consumer articles associated therewith, for dispensing an active composition into the surrounding space. The device includes an assembly containing a reservoir holding the active liquid to be diffused into the surroundings and a wick-/emitting member structure composed of a wick member and an emitting/diffusion member, the latter having an evaporative surface to be directly exposed to the surrounding space when the device is activated, the assembly being housed in a casing or carried by a supporting frame, the device further including a pivoting member fixed on the casing or on the supporting frame to allow a swinging motion of the assembly and thus forced evaporation of the active volatile whenever desired.

17 Claims, 12 Drawing Sheets

(56) References Cited

U.S. PATENT DOCUMENTS

| | | | |
|---|---|---|---|
| 7,441,755 B2 | 10/2008 | O'Leary et al. | 261/104 |
| 2004/0250962 A1* | 12/2004 | Hart et al. | 159/7 |
| 2005/0140032 A1 | 6/2005 | O'Leary et al. | 261/104 |
| 2006/0043619 A1 | 3/2006 | Brown et al. | 261/19 |
| 2006/0071092 A1 | 4/2006 | Harris, Jr. | 239/44 |
| 2008/0217426 A1 | 9/2008 | Brown et al. | 239/45 |

OTHER PUBLICATIONS

International Search Report and Written Opinion of the International Searching Authority mailed Mar. 3, 2010 for Application No. PCT/IB2009/055743 filed on Dec. 14, 2009.

* cited by examiner

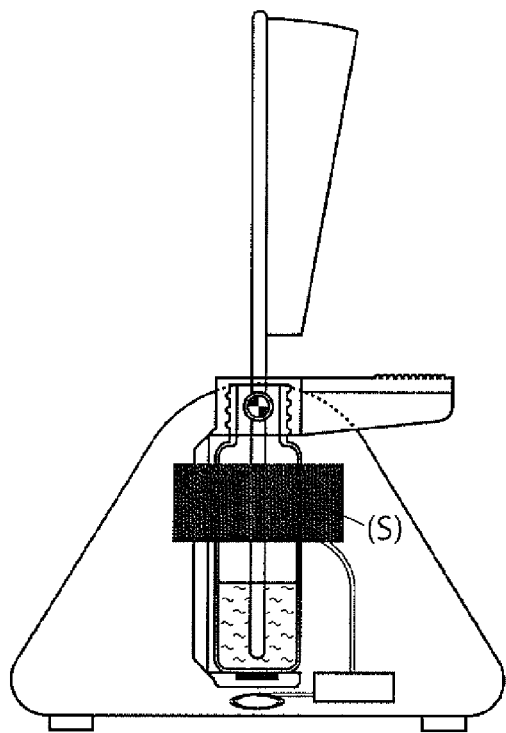 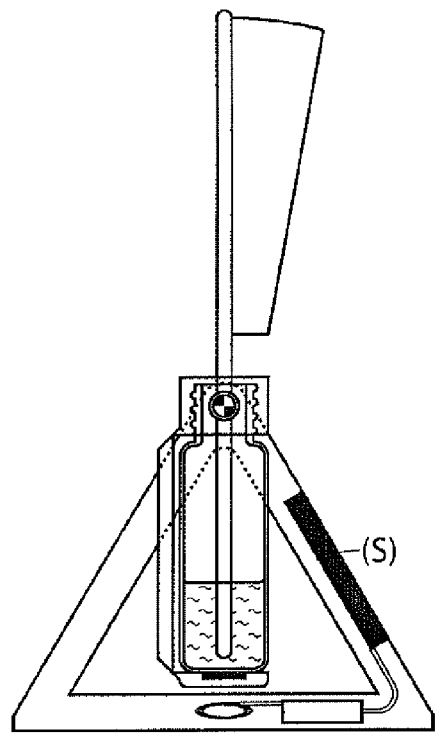
Figure 8a)   Figure 8b)
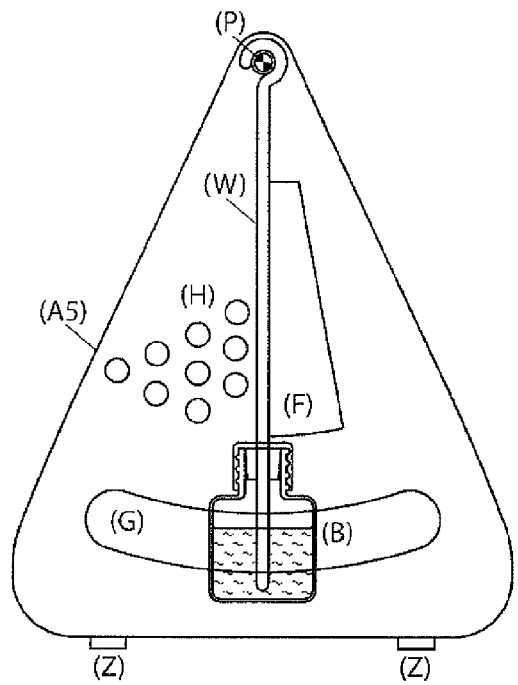 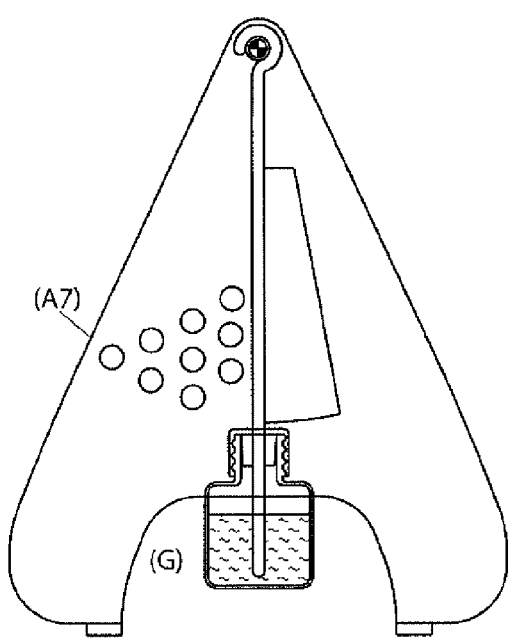
Figure 9a)   Figure 9b)

ical Field

The present invention relates to the field of perfumery and more precisely it concerns a device for dispensing an active volatile substance into its surroundings, particularly in an enclosed atmosphere. The device of the invention is an air-freshener device comprising a reservoir for containing an active liquid, namely with a specific volatility, and containing a substance that one desires to disseminate into the atmosphere, and at least one wick/emanating structure composed of a part able to soak in the liquid volatile and be impregnated therewith and an emitting part, the latter having an evaporative surface exposed to the surrounding space, and optionally a specific absorbency and weight per unit of said evaporative surface. At least a part of the wick/emanating structure is intended for connection to means capable of engaging said part into a swinging movement around a pivoting axis, and thus force enhanced evaporation of the volatile substance from the evaporation surface of the emitting part, relative to the evaporation that would have been observed in the absence of such means.

Prior Art and Problem to be Solved

Devices for dispensing an active volatile liquid in the surrounding space have been known for a long time. One type of such devices is the so-called wick-based type devices, which all comprise a reservoir, a wick plunged in a volatile liquid that is intended to be diffused from the air freshener and an emanating body or surface from which the active liquid evaporates.

Many air-freshener devices of the wick type have been described in the prior art. Although many such devices work by unforced evaporation only, it is often desirable to increase the latter by providing evaporation forcing means, for example an external fan or other mechanical means increasing ventilation and thus forcing evaporation of the volatile substance from the emitting surface, or yet means providing for electrical heating of the evaporating surface of the porous wick/emitting member element(s).

Forced ventilation of the emanating surface has required in the past the use of separate parts, particularly fans, that are battery or electrically powered. Typical recent examples of such devices are described, amongst others, in patent documents WO 2005/030277 A1 and US 2006/0043619 A1. In the first of these, there is described a device provided with an electrically-powered fan acting on an evaporation surface that is essentially planar and has an orientation generally parallel to the direction of the forced ventilation provided by the fan, whilst the teaching of US 2006/0043619 is representative of more conventional fan operated air-fresheners.

Many other examples of fan operated devices can be found in the prior art but they all require rotating parts that are independent and separate from the wick/emitting structure and which increase the cost of the device relative to those which rely on unforced evaporation. The present invention aims at dispensing with such separate moving parts, whilst still providing for enhanced evaporation of the volatile substance to be dispensed into the atmosphere.

The device of the present invention comprises means allowing a direct swinging movement, around a pivot mounted on the housing or supporting structure of the device, of the evaporating surface for the volatile substance, thus dispensing with the use of a separate fan to increase ventilation of said surface.

To the best of our knowledge, the prior art has never taught or suggested such a solution to the problem of increasing ventilation of the evaporation surface in a wick type air-freshener. U.S. Pat. No. 6,103,201, to Dennis E. Green, has taught the use of a rotor made of scent-bearing material and adapted to be connected to room ventilation systems, but such a rotor cannot be connected to a reservoir containing the volatile substance so as to allow constant replenishing of the evaporation surface in volatile material, necessary for a linear and sustained release thereof over time, during the normal and/or forced evaporation periods.

The present invention aims at improving over all the known devices by providing an air freshener that is efficient in delivering a constant and linear amount of active composition over the lifetime of the device and is particularly adapted to be used with substantially non-aqueous volatile compositions, thus dispensing the use of large amounts of surfactants, and which requires a smaller number of parts to be manufactured and assembled, as compared to other movement actuated air fresheners having an enhanced capability of volatile substance evaporation. Moreover, the claimed device has also the advantage of being adapted to manual or powered activation, particularly solar panel powered, and is therefore a device that fulfils requirements of energy sustainability.

DESCRIPTION OF THE DRAWINGS

FIGS. 8a) and b) are elevated views, partially in cross section, of solar panel powered devices of the invention, provided with a supporting frame in lieu of a casing or housing element.

FIGS. 9a) and b) are elevated views, partially in cross section, of manual activation device variants wherein the pivoting axis is fixed above the wick/emitting structure assembly and the pivot means are attached to the top of the device's housing, the latter being provided with a gap on one of its faces allowing external access to the reservoir allowing it to be manually moved into the swinging movement.

DESCRIPTION OF THE INVENTION

Figure 1:
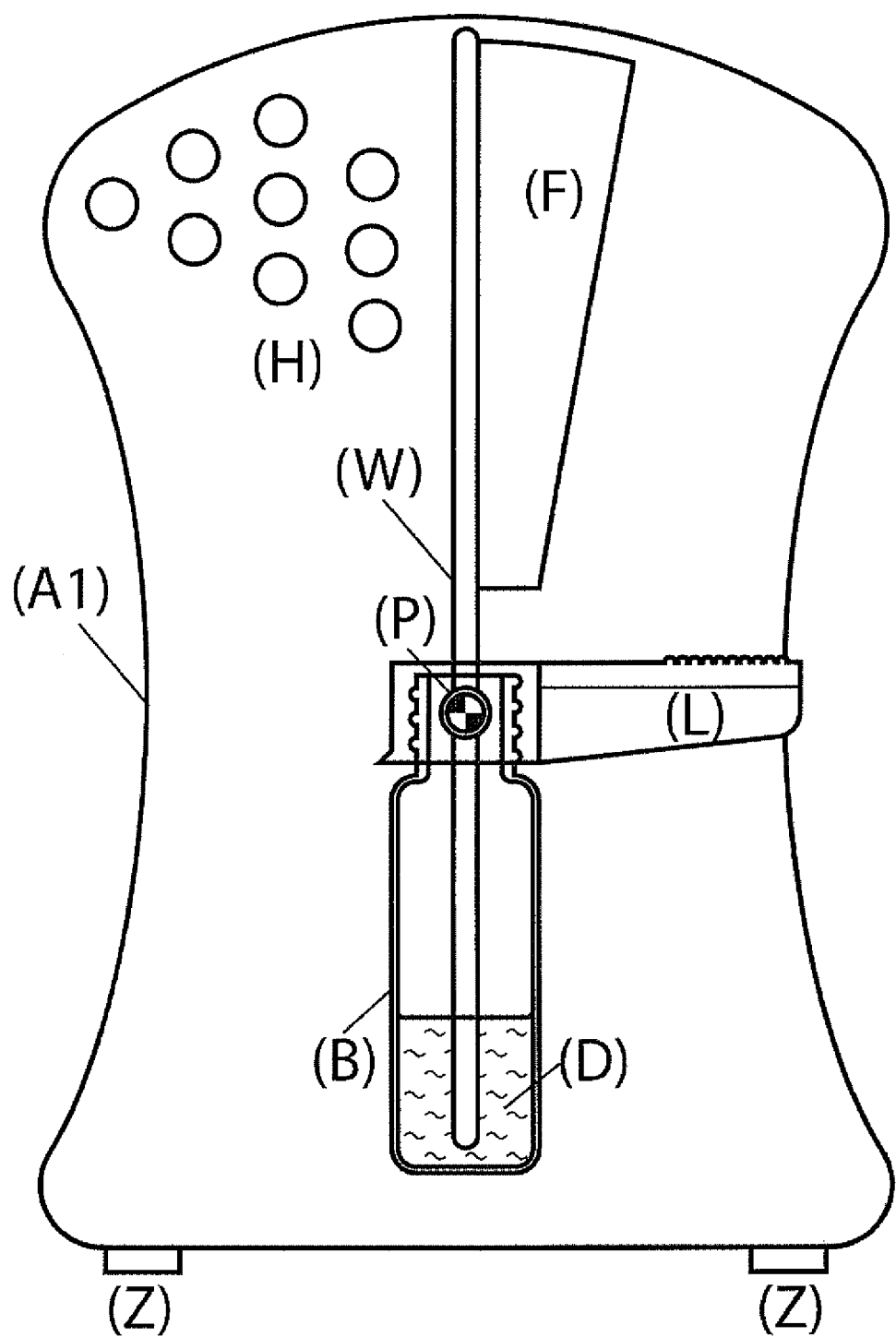
FIG. 1 is an elevated view, in cross section, of one embodiment of the device according to the invention, showing the various parts of a device that is intended for manual activation and wherein the pivoting axis is located between the reservoir and the wick/emanating structure.

The aim of the present invention is to provide an air freshener of the wick type able to diffuse an active volatile liquid in the surrounding space, rooms, cupboards or other enclosed spaces, possibly provided with a light source, the device having an essentially linear performance when at equilibrium, i.e. diffusing a volatile substance at approximately constant rate during each period of unforced or forced evaporation of the active volatile.

This is achieved by a device for dispensing an active volatile substance into the surrounding atmosphere, provided with means for forced ventilation of an evaporation surface impregnated with said volatile substance, said device comprising a housing or a supporting frame and an assembly of:
a) a reservoir containing the active volatile substance and having an upper part equipped with an opening optionally covered with a cap;
b) at least one emanating member carrying said evaporation surface and formed of a material capable of being impregnated with said active volatile substance upon activation of the device and of allowing evaporation thereof into the device's surroundings;
c) at least one wick member formed of, or carrying, a porous material part capable of being impregnated with said active volatile substance, said wick member being adapted to be lodged in the device through the opening of the reservoir's upper part in a position allowing it to be impregnated with the volatile substance and to be in contact with the emanating member;
wherein, upon activation of the device, the emanating member and the wick member are lodged in the device in a position allowing the wick member to be in contact with the active volatile substance and to cause the emanating member to be impregnated therewith, the means for forced ventilation of the evaporation surface comprising a pivot fixed to the housing or supporting frame, the assembly being arranged on the pivot in a manner allowing a swinging movement thereof around the pivoting axis for a period of time, so as to cause forced ventilation of said evaporation surface of the emanating member, the swinging movement of the assembly being triggered by manual, mechanical or electronically powered displacement of one or more assembly components.

By an "active volatile liquid, substance or material", or a "volatile liquid, substance or material", all of which are used here interchangeably, we mean here a liquid that is at least partially volatile, i.e. can evaporate under atmospheric pressure and normal room temperatures typically comprised between 15 and 35° C., and which is able to impart a benefit to the surroundings of the device according to the invention.

The designations "emanating", "emitting" and "diffusing", all applying to the member, part or piece of the wick-emanator structure from which the liquid typically evaporates into the surroundings, shall be used herein interchangeably, to designate the part of the air-freshener device, or of its wick/emitting structure, that extends from the opening of the reservoir, containing the volatile substance to be diffused, to the exterior of said reservoir and is exposed to the air surrounding the air freshener. This component of the wick/emitting structure assembly possesses an evaporative surface or area defined hereinafter and can assume any shape compatible with the definition of that area. It may be formed of one or several elements.

By "wick" or "wick member" it is understood here essentially the part of the wick/emitting structure of the device which is plunged in the liquid contained in the reservoir, once the device is activated. According to certain embodiments of the device however, the wick may also extend towards the exterior of the reservoir and provide a supporting structure for fixing the emanating member and improving the contact between the two, so as to properly impregnate the latter with volatile substance.

Moreover, according to alternative and advantageous embodiments of the invention, the wick and emitting member may be part of a same single piece or member, forming the wick/emitting structure, one end, typically the lower end, of said piece being plunged in the active substance when the device is in operation after activation thereof, and the other end, generally the upper part, of said single piece or member extending from the opening of the vessel containing the active substance, so as to be in contact with the surroundings of the air freshener device and be able to diffuse the active substance.

This single piece embodiment of the wick/emitting structure is particularly advantageous as it allows the use of a plurality of such single pieces in the air freshener, thus allowing to increase the diffusing power of the latter and the replacement of part of its diffusing surface without replacing the whole, if desired.

Preferably, the wick part, as well as the whole wick/emitting assembly, is made of the same material as the emitting part.

According to specific embodiments of the device of the invention, there is further provided a housing or casing which comprises means to allow diffusion of the active volatile into the device's surroundings upon its activation. This housing or casing may be of any shape, provided that its design and dimensions allow the free swinging movement of the emanating member or of the assembly as a whole around the pivot axis or bearing, and the lodging therein of the assembly formed by the reservoir and the wick/emitting structure, in a position allowing its manual, mechanical or electronic actuation.

The housing or casing may be replaced by an open supporting frame for the assembly, to which frame the pivot is fixed—this other embodiment makes it possible to completely expose the emitting member to the surrounding air and may also provide for visibility of the reservoir so as to observe when the liquid needs to be replaced.

Of course, the housing may also be provided with gaps or openings of a size sufficient to allow similar visibility of the reservoir and exposure of the evaporation surface to the surroundings.

The pivot means according to the invention can consist of a cylindrical pin and be lodged for example in the cap of the reservoir, or they can be entirely lodged in the casing or supporting frame of the device. They may also consist of a shaft arranged in a similar manner. The essential parameter is that the pivot is engaged with at least one element of the reservoir, the wick and/or the emitting member assembly, in such a manner as to allow swinging movement of the latter around the pivot axis.

The swinging movement of the assembly or a part of it can be manually, mechanically or battery/electrically powered, and advantageously via a solar powered mechanism. The latter embodiment of the invention has obvious energy supply advantages, as well as allowing its use even in places where electrical energy is not readily available.

Alternatively, a wind up or spring type mechanism may also be used to power the swinging movement by mechanical means. Battery or electricity mains driven powering is also appropriate.

By the "active volatile substance, composition or liquid" contained in the reservoir it is meant herein a liquid composition which is at least partially volatile, i.e. can evaporate, and which is able to impart a benefit to the atmosphere or space surrounding the device.

According to advantageous embodiments of the invention, the active volatile is selected amongst the group of fragrance, deodorizing, sanitising, insect repellent compositions, and their mixtures. It is clear however that other volatile or partially volatile substances may be diffused into the atmosphere from the device of the invention, provided they are adapted to impregnate and diffuse from the materials, namely porous materials, forming the wick, respectively emanating, members.

The reservoir chamber is a vessel or bottle which has the function of storing the active volatile liquid composition or, as also referred from now on, the "active composition", which is preferably non-aqueous. Prior to activation of the device, the reservoir contains an initial amount of liquid active substance and, after activation, the remainder thereof which has not yet, at any given moment in time, been absorbed on the wick/emanating member structure and diffused.

The invention also relates to specific embodiments wherein the wick member is lodged within a guiding or supporting structure disposed within the housing, possibly a shaft type structure that also supports the emitting/evaporation member. This wick member guiding or supporting structure is preferably vertically disposed within the housing or frame, and may be able to engage into a swinging movement from one side of the pivot to the other when forced evaporation is desired.

The reservoir will typically be provided with means to prevent evaporation of the active composition from the reservoir before activation thereof. According to preferred embodiments, the reservoir's opening carries a lid or barrier formed of foil and hermetically fastened thereto before activation of the device. The foil is intended for removal upon activation, and possibly for being perforated by the wick member or a wick-guiding member. This barrier then has the function of preventing evaporation of the volatile composition before activation of the device and is removed or perforated when the device is in use to diffuse the active volatile.

The reservoir may also carry a cap assembly. The latter may advantageously carry the pivot around the axis of which the assembly swings between the two extreme positions of its movement.

According to advantageous embodiments, the emanating or emitting member will be arranged on a support structure, namely a shaft, provided with a hollow cavity adapted for lodging the wick member. Alternatively, the wick member itself is formed of a long cylindrical rod having a part extending vertically above the reservoir, and is provided with supporting means for the emanating member. Details of the manner in which the latter may be realized are presented in the examples described further on, but also as taught in International patent application WO 2006/061803, owned by the present applicant, and all variants of the wick/emanating member relative arrangement described in this document that are compatible with the swinging movement according to present invention, and adapted to function in the manner described herein, are hereby included by reference, as it is trivial for the skilled person to incorporate them in the device here-claimed.

As previously indicated, the emitting and wick members, or their single piece assembly, may be lodged within the device's housing. They are preferably coaxially arranged (although such an axis does not have to be vertically arranged) when lodged within the housing's structure. Typically, the supporting structure for the emitting member will be part of the wick, when the two do not form a single piece.

Whenever a device housing or casing is provided, its shape can however be any, provided that it is adapted to allow free swinging movement of the assembly lodged inside the housing. It may be formed of one or two elements, as taught in WO 2006/061803, the relative arrangement of the two elements being such that it does not interfere with the swinging ability of the active substance absorption/evaporation assembly.

Of course, it is also possible to have a device according to the invention that is not provided with a housing. Since the emanating and wick members are generally only put into contact with the active volatile substance contained in the reservoir upon activation of the device, a housing is not needed for the purposes of stopping evaporation thereof before use, and can be dispensed with in at least some of the embodiments of the invention. An open frame to support the pivot and the wick/emanating member assembly may be a perfectly convenient and advantageous alternative.

As previously indicated, the wick/emanating member structure may be formed of a single piece, or of at least two separate pieces arranged in such a manner that the emanating part is optimally exposed to the increased flow of air generated by the swinging movement, when forced evaporation is desired.

There are therefore many ways in which these two elements can be designed and possibly lodged in a housing or frame. In preferred embodiments, the wick or wick-guiding structure may be provided with grooves or dents carved on its surface and shaped in a form adapted to accommodate tightly the element or elements of the emanating member, so as to form a superstructure such as taught for example in U.S. Pat. No. 7,441,755, granted to the applicant, provided that at least the emanating member can move as taught herein.

According to the invention, the emanating part may for example be disposed on the wick or guiding shaft structure in a manner allowing its deformation or rotation around the vertical axis of the latter, as a result of the increased air flow acting on the evaporation surface when the assembly is engaged into the swinging movement.

In one such embodiment, the diffusing surface may be in the shape of a variety of fins, which are fitted onto grooves of complementary shape to that of the lower part of the fin, so as to allow tight lodging of the latter within the groove, carved on the upper face of a lid intended to cover the opening of the reservoir. The whole fin assembly can thus form a star-shaped structure. It is clear that the fins can alternatively be fixed into grooves carved vertically in the shaft or wick axis structure to achieve a similar effect.

The shape of the emanating member can however be any, provided it is compatible with a swinging movement susceptible of causing enhanced evaporation of the volatile substance from the emitting member's evaporation surface.

Likewise, the wick member of the air freshener can assume any form that is compatible with the possibility of engaging with the emitting member in order to allow its impregnation with liquid. In most of the embodiments represented below, the wick is a thin cylinder, forming a rod-like structure, possibly hollow, on which the emitting member can then be mounted in a manner allowing it to move relative to the wick part plunged in the reservoir, when accelerated evaporation is desired. The shape of the emitting member may also be flat.

According to non-manually activated embodiments of the device, the latter comprises as an essential element powering means preferably actioned via an electrical current induced on a solenoid or coil which is capable of attracting or repelling a magnet connected to the assembly comprising the reservoir and the wick/emitting structure. The solenoid may be part of a printed circuit board provided in the housing or frame of the device, which may also comprise a battery externally powered.

When solar powered means are desired, the air freshener device of the invention may be equipped with a solar cell or panel capable of accumulating energy from day or sunlight, or from a source of artificial light, connected to the battery, as shown specifically in some of the examples presented further on.

If the powering means are mechanical, one can use typically a wind-up, clock type mechanism to drive the swinging movement. The latter is then directly initiated by the user, through winding of the mechanism.

The invention also includes packaged devices, wherein the reservoir, generally containing the active volatile substance, is hermetically closed as described above and packaged separately from the other parts of the device. Such an embodiment of the invention presents the advantage of being re-chargeable, the supply of active volatile being able to be substituted by a new filled reservoir, or an assembly of reservoir and wick/emitting structure, when the prior used one is empty. Moreover, it is then also possible to acquire the device in different pieces, at different moments in time and to assembly it upon use.

For example, the reservoir or container holding the active volatile substance is provided in a separate packaging from that of the emanating member, or even from the separate wick/emanating members' packaging or packagings.

The reservoir will be typically hermetically closed and caped during storage. The wick/emanating members will be shaped so as to allow the user to assemble them together, if they are not of a single piece, and then lodge the structure thus obtained on the reservoir opening in such a manner that the absorbing surface of the wick is plunged into the active substance when the device is activated. For example, the reservoir may be provided with a foil hermetically closing its opening, and the wick member provided with a pointed extremity able to perforate the foil to allow immersion of the wick into the volatile. Perforation of the hermetic barrier of foil may be carried out by the user or forced by movement of the housing in a generally known manner.

Once the device is in the active position, activating the movement around the pivot via for example a lever, manually or electrically powered, will provide for the desired swinging movement, and the user will therefore be able to use unforced or forced evaporation, as wished.

The emanating and wick members may not be part of a same piece or structure, and it is then possible to have the wick completely plunged inside the reservoir's liquid before use and to force the emanating member to come into contact with the wick upon activation of the device, to thus be impregnated with active liquid to be diffused over time from its evaporative surface.

In general, the essential parts of the device are formed by the reservoir containing the volatile composition, a barrier to prevent evaporation of the latter prior to activation of the device, an absorption/diffusion member or members, capable of being impregnated with the composition and of diffusing it into the surroundings once the device is activated, the supporting structure for the emanating member comprising an element, possibly the wick or a part thereof, shaped in a form allowing a swinging movement thereof around a pivoting axis defined by the pivot means. The latter may be integrated in the guiding means for the wick/emanating member structure, namely the cap of the reservoir, or be separately fixed on the housing or frame of the device, as exemplified below.

Features of the Wick and Diffusing Members, as Well as of the Reservoir, Possibly Forming an Assembly, and of the Active Volatile Liquid to be Diffused The device according to the present invention comprises a wick/emitting structure of a similar type to that described in the above-mentioned U.S. Pat. No. 7,441,755.

According to the present invention, the important features of the wick/emitting structure are that:
i) the emitting part or member must have a high surface area relative to the amount (mass or volume) of liquid absorbed by the wick and emitting part;
ii) the liquid contained in the reservoir is a concentrated active volatile, preferably fragrance, and can therefore be used in relatively small amounts as compared to prior known water based compositions;
iii) the volatile liquid is absorbed over the entire surface of the emitting part soon after activation
iv) the wick and emitting parts are constructed so that the maximum amount of liquid absorbed in the wick and emitting parts (that is when the liquid is absorbed over the entire surface of the emitting part) is less than about 20% by weight of the initial (before activation of the device) amount of volatile liquid in the device The liquid contained in the reservoir shall typically be a concentrated volatile composition, preferably a perfume. Solvents (other than water) are useful to control and adjust the evaporation characteristics of the perfume. It is also possible to formulate the perfume without solvent at all by adjusting evaporation through selection of the appropriate perfume raw materials used.

The amount of solvent in the active liquid substance is less than 75% w/w, preferably between 15% and 60% w/w, most preferably between 25% and 50% w/w.

The amount of liquid composition initially in the device is between 5 g and 30 g, more preferably between 7 g and 21 g, most preferably between 10 g and 18 g.

The liquid should absorb over the entire surface of the emitting part soon after activation of the device and the mass of liquid absorbed in the emitting part should remain approximately constant until the point at which there is insufficient volatile liquid remaining in the reservoir to replenish the volatile liquid that has evaporated from the surface of the emitting part. Absorption should be complete within 24 hours of activation, more preferably within 12 hours, more preferably within 4 hours, most preferably within 2 hours.

The mass of active volatile liquid absorbed by the wick/emitting members assembly remains more or less constant during the lifetime of the air freshener device, since the mass evaporated from the emitting part is compensated by the replenishing of the evaporating surface via the wick, until the amount of liquid remaining in the device is no longer enough to saturate the surface of the emitting part.

According to the invention, the maximum amount of liquid absorbed by the wick and emitting parts assembly is less than 20% by weight of the total amount of liquid initially in the device, preferably between 5 and 15% by weight, most preferably between 8 and 13% by weight of the total weight originally in the reservoir, before activation of the device.

Preferred embodiments of the device therefore have the following characteristics:

Mass of perfume in the reservoir, before activation, comprised between 7 g to 13 g Solvent dosage in the active composition is comprised between 25 and 50% by weight of the total liquid weight Mass of liquid composition in the reservoir, before activation, is comprised between 10 g and 18 g Amount of liquid absorbed in wick and emitting parts=8% to 13% by weight, of the initial weight of the liquid in the device, and it remains approximately constant until the amount of liquid remaining in the device is less than the initial amount absorbed by the wick/emitting member assembly.

From the above, the mass of liquid that will be typically absorbed will be from 0.8 g to 2.34 g.

The emitting part can also be characterized as comprising a surface area of between 50 cm$^2$ and 400 cm$^2$, preferably between 75 cm$^2$ and 300 cm$^2$, most preferably between 100 cm$^2$ and 200 cm$^2$.

For a surface area of the emitting part between 100 cm$^2$ and 200 cm$^2$, a preferred range according to the invention, the ratio of that surface area to the mass of liquid absorbed by the wick/emitting part is between 20 cm$^2$/g and 200 cm$^2$/g, preferably between 30 cm$^2$/g and 150 cm$^2$/g, most preferably between 40 cm$^2$/g and 100 cm$^2$/g.

Preferred materials of which the emitting member can be made are cellulose derivatives, e.g. papers, moulded ceramics, sintered or porous plastics, or even mixed sintered materials such as a sintered plastic and a sintered metal. When using mixed materials for the emitting member or part, it is important that the two materials have identical characteristics relative to the parameters affecting air freshener functionality (pore volume, pore size, absorption capacity, thickness, surface area, volume).

Preferred papers are those currently used as filter paper and having a particle retention size comprised between 3 μm and 30 μm, such as those commercially available from Whatman International Ltd., UK as Filter Paper N° 1, 3, 4 or 113. Other preferred papers include those used as fragrance testing papers and blotters for fragrance sampling, such as those commercially available from Orlandi Inc., USA.

In the case of sintered or porous plastics, preferably such materials will have a porous size comprised between 5 μm and 200 μm and is based on high density polyethylene, ultra high molecular weight polyethylene or polypropylene. Examples of such materials are commercially available, e.g, under the tradename Vyon® T (origin: Porvair Technology Ltd, UK).

The preferred diffusion materials used as the emanating surface or emitting member part of the absorption/diffusion structure have the following characteristics:

| Description | Thickness (mm) | Weight (g/m$^2$) | Liquid absorbed (g/cm$^2$) |
| --- | --- | --- | --- |
| Whatman No. 1 filter paper | 0.18 | 87 | 0.005-0.010 |
| Whatman No. 3 filter paper | 0.39 | 185 | 0.012-0.024 |
| Whatman No. 4 filter paper | 0.21 | 92 | 0.008-0.016 |
| Whatman No. 113 filter paper | 0.42 | 125 | 0.015-0.030 |
| Vyon ® T (sintered plastic) | 1.50 | 780 | 0.050-0.080 |

As described above, the emitting member may comprise one or more emitting bodies in contact with each other, in general from one to six emitting bodies being used.

The wick member is intended to absorb a part of the active composition contained in the reservoir and transport the latter to the emitting member, from which it can evaporate into the surrounding space of the invention's device. This part of the absorbing/diffusing structure of the device is constructed so that the rate at which the active volatile liquid is supplied from the reservoir to the emitting part is sufficient to will be a hollow cylinder capable of absorbing enough liquid from the reservoir to ensure that the diffusing/evaporation surface of the emitting part is constantly saturated in liquid to be diffused, until there is insufficient amount of liquid remaining in the device to ensure such saturation.

The wicking part or wick may be made of organic and inorganic materials. Examples for appropriate inorganic materials include porous porcelain materials, moulded ceramics, glass fibers, or asbestos, in combination with a suitable binder such as, for example, gypsum or bentonite. It is also possible to prepare wicks from powdered mineral materials, such as, for example, clay, talc, kieselguhr, alumina, silica or the like, alone or in combination with, for example, wood flour, carbon powder, or activated carbon, using an appropriate glue. Organic materials include felt, cotton, pulp, woven and non-woven cotton fibers, synthetic fibers, cellulose derivatives, e.g. papers, and woven and non-woven sintered or porous plastics, as well as wood, possibly covered with plaster. Other details and specific examples relating to these embodiments of the invention can be found specifically in the description of prior mentioned U.S. Pat. No. 7,441,755, prior published as US 2005/0140032, the contents of which are hereby incorporated by reference.

More preferred embodiments comprise wicks formed of porous natural paper material, namely pressed paper.

It is clear from the above that the wick and emitting parts of the absorbing/diffusing member or piece may be made of the same material, forming a single piece that absorbs the active substance via its part that is plunged in the latter and diffuses the active substance vapours via its emitting part, that extends beyond the opening of the vessel and is in contact with the air freshener surroundings. This particular embodiment of the invention makes it possible to use a plurality of wick/emitting pieces of a variety of shapes, in particular rod, oval or flat shaped reeds or sticks, as exemplified below, possibly in cylindrical, filled or hollow form, so as to comply with the surface area, and surface area to mass of liquid absorbed ratio cited above.

For emitting members or parts that are not flat shaped, the evaporative surface thereof is calculated in a generally known manner, by the usual formulae applying to the surface of cylindrical or other 3-dimensional forms and complies with the above-mentioned definitions. The surface area and volume dimensions of this emitting part are such that less than about 20% of the entire volume of liquid initially contained in the reservoir is enough to entirely saturate the diffusion surface in volatile liquid, when the device is activated and starts diffusing vapours into its surroundings. In this manner, only the amounts that are evaporated from the diffusing surface are thereafter regularly replenished via the wick part of the absorbing/emitting member assembly, and the diffusing surface is kept saturated in liquid throughout the lifetime of the device. The evaporation of the active volatile substance is therefore entirely controlled by the evaporation surface characteristics. This makes it possible to use far lower volumes of concentrated active volatile substance, as compared to previously known wick-type devices, and renders the device economically viable, even when using concentrated (i.e. essentially water free) hydrophobic liquids, such as concentrated perfumes.

According to more preferred embodiments of the invention, less than 20% by weight, and preferably an amount comprised in the range of 5% to 15% by weight, and most preferably an amount comprised in the range of 8% to 13% by weight, of the initial total weight of liquid contained in the reservoir, is absorbed by the wick and emitting surface upon activation of the device, to initially completely saturate this emitting surface and thus promote replacement of the absorbed liquid as the latter evaporates from the surface into the surroundings. Wick and emitting member assemblies wherein the emitting part has a surface area comprised in the range from 100 $cm^2$ to 200 $cm^2$, and wherein the ratio of the emitting part surface area to mass of liquid absorbed by the wick and emitting part assembly is comprised in the range from 40 $cm^2/g$ to 100 $cm^2/g$, are embodiments of the invention perfectly adapted to provide the effect described.

The reservoir, and possibly a cap therefore, are formed of materials compatible with the active composition and totally impermeable to the vapours of the latter. Preferably the reservoir chamber is made of a transparent or translucent material, so that a consumer can visually monitor the level of the active composition present in the reservoir chamber, and therefore know when the device according to the invention has to be replaced because exhausted. Typical reservoirs shall contain from 5 g to 30 g of liquid, more preferably from 7 g to 21 g, most preferably from 10 g to 18 g.

Suitable materials for the reservoir chamber and the reservoir chamber lid or cap, include glass, injection or thermoform moulded materials such as those obtainable from polymers like polyethylene, polypropylene, polystyrene, polyvinyl chloride, polyvinyl acetate, polyamide, polyacrylamide, polymethylacrylate, and the like.

It is also understood that the reservoir and the cap can be part of a single body, typically a moulded piece, which may also incorporate the means to manually engage the assembly into a swinging movement around a pivot, also possibly incorporated in the same moulded piece.

Preferred Materials and Characteristics of the Liquid Composition to be Diffused According to a preferred embodiment of the invention, the composition to be contained in the reservoir is non-aqueous.

By a "non-aqueous active volatile liquid composition" it is meant here an active volatile liquid composition which is essentially devoid of, or contains only marginal amounts of, water, e.g. one may cite as example a composition which contains at most 10%, and more preferably less than 5%, of it total weight, of water.

A useful active composition is preferably also surfactant free.

The active composition contains at least one active ingredient. Said ingredient is capable of imparting a benefit to the surrounding space or enclosed space in which the device is activated, and forming an active volatile material, and may be accompanied by optional ingredients which can be beneficial to said active volatile material. In other words the active composition contains an active volatile material, comprising at least one ingredient, and optionally one or more ingredients selected from the group consisting of solvents, thickeners, anti-oxidants, dyes, bittering agents and UV inhibitors.

As the active volatile material, there can be used preferably a perfume. Other suitable active volatile materials can be deodorizing or sanitizing agents or insect repellents or any other active materials capable of imparting perceptible and desirable benefits to the quality of the air into which they are diffused.

As perfume there can be used any ingredient or mixture of ingredients currently used in perfumery, i.e. capable of exercising a perfuming action, meaning modifying or imparting the odor of the surrounding air. This means that a malodour counteracting composition, capable of reducing or suppressing a large variety of malodors, such as body malodour, tobacco malodour, kitchen or bathroom malodour for example, are also understood herein as being comprised in the "perfume", "fragrance" or "perfuming composition" definition. Often, such a perfuming composition will be a more or less complex mixture of ingredients of natural or synthetic origin. The nature and type of said ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. Many are known to possess malodour counteracting and/or antibacterial activity so that, in addition to being capable of perfuming, and thus imparting a pleasant smell to, the surrounding air, they also help purify and sanitize the latter, and/or remove any malodour (i.e. unpleasant smell) thereof.

Natural oils such as lavender, cedar, lemon and other essential oils and extracts are particularly preferred for advantageous embodiments of the invention.

Although special mention has been made hereinabove of the perfuming effect that can be exerted by the devices of the invention, the same principles apply to analogous devices for the diffusion of deodorizing or sanitizing vapours, the perfume being replaced by a deodorizing composition, an anti-bacterial, an insecticide, an insect repellent or an insect attractant, or a so-called mothproofer device. By the term "sanitizing vapours", we refer here not only to the vapours of those substances which can enhance the degree of acceptance of the air surrounding the observer, but also to those substances which can exert an attractant or repellent effect towards certain species of insects, for instance towards houseflies or mosquitoes, or else, which can have bactericide or bacteriostatic activity. It goes without saying that mixtures of such agents can also be used.

The total amount of active volatile material in the active composition may be comprised between 25% and 100%, preferably between 40% and 85%, most preferably between 50% and 75% by weight, of the weight of active composition.

As anticipated above, the active composition may also contain some optional ingredients acting as, for example, solvents, thickeners, anti-oxidants, dyes, bittering agents and UV inhibitors.

As non-limiting examples of useful UV-inhibitor ingredients, one can cite benzophenones, diphenylacrylates or cinnamates such as those available under the trade name Uvinul® (origin: BASF AG).

The total amount of UV-inhibitors present in the active composition may vary between 0.0% and 0.5%, preferably between 0.01% and 0.4%, the percentages being relative to the total weight of the active composition.

The presence of one or more solvents may be useful to have a single-phase or dual phase liquid and/or to modulate the speed of evaporation of the active material into the surrounding air. Said solvents may belong to the families of isoparaffins, paraffins, hydrocarbons, namely glycols, glycol ethers, glycol ether esters, esters or ketones.

Examples of suitable commercially available solvents are known under the tradename Isopar® H, J, K, L, M, P or V (isoparaffins; origin: Exxon Chemical), Norpar® 12 or 15 (paraffins; origin: Exxon Chemical), Exxsol® D 155/170, D 40, D 180/200, D 60, D 70, D 80, D 100, D 110 or D 120 (de-aromatised hydrocarbons; origin: Exxon Chemical), Dowanol® PM, DPM, TPM, PnB, DPnB, TPnB, PnP or DPnP (glycol ethers; origin: Dow Chemical Company), Eastman® EP, EB, EEH, DM, DE, DP or DB (glycol ethers; origin: Eastman Chemical Company), Dowanol® PMA or PGDA (glycol ether esters; origin: Dow Chemical Company) or Eastman® EB acetate, Eastman® DE acetate, Eastman® DB acetate, Eastman® EEP (all glycol ether esters; all origin: Eastman Chemical Company) or yet 3-methoxy-3-methyl-1-butanol, also known as solvent MMB and available from a variety of suppliers.

Other examples of solvents useful to the invention are dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

Preferred solvents include Dowanol® DPM, DPnB, PGDA or DPnP, as well as 3-methoxy-3-methyl-1-butanol.

The total amount of solvents present in the active composition may vary between 0.0% and 75%, preferably between 15% and 60%, most preferably between 25% and 50% by weight, the percentages being relative to the weight of the active composition. Preferred perfuming compositions will comprise at least 40% by weight of perfume and not more than 60% by weight of any such solvents.

Preferably, at least 60% of total weight of the active composition is made of ingredients having a vapour pressure comprised between 4 Pa and 270 Pa, said vapour pressure being measured at 20° C. and a pressure of 760 mmHg. The described requirement in the formulation of the active composition ensures that a relatively constant composition is maintained over the lifetime of the device and that said active composition evaporates at a relatively steady rate during the life of the product.

Most preferably, at least 80% of total weight of the active composition is made of ingredients having a vapour pressure comprised between 4 Pa and 270 Pa.

As non-limiting examples of useful antioxidant ingredients, one can cite the sterically hindered amines, i.e. the derivatives of the 2,2,6,6-tetramethyl-piperidine, such as those known under the tradename Uvinul® (origin: BASF AG) or Tinuvin® (origin: Ciba Speciality Chemicals), as well as the alkylated hydroxyarene derivatives, such as butylated hydroxytoluene (BHT).

The total amount of antioxidants present in the active composition may vary between 0.0% and 10%, preferably between 1% and 4%, the percentages being relative to the weight of the active composition.

Dyes are other optional ingredients of the active composition. Suitable dyes are oil-soluble and can be found in the Colour Index International, published by The Society of Dyers and Colourist. Non-limiting examples of suitable dyes are derivatives of the anthraquinone, methine, azo, triarylmethane, triphenylmethane, azine, aminoketone, spirooxazine, thioxanthene, phthalocyanine, perylene, benzopyran or perinone families.

Examples of such dyes which are commercially available are known under the tradename Sandoplast® Violet RSB, Violet FBL, Green GSB, Blue 2B or Savinyl® Blue RS (all anthraquinone derivatives; origin: Clariant Huningue S.A.), Oilsol® Blue DB (anthraquinone; origin: Morton International Ltd.), Sandoplast® Yellow 3G (methine; origin: Clariant Huningue S.A.), Savinyl® Scarlet RLS (azo metal complex; origin: Clariant Huningue S.A.), Oilsol® Yellow SEG (monoazo; origin: Morton International Ltd.), Fat Orange® R (monoazo; origin: Hoechst AG), Fat Red® 5B (diazo; origin: Hoechst AG), Neozapon® Blue 807 (phtalocyanine; origin: BASF AG), Fluorol® Green Golden (perylene; origin: BASF AG).

The total amount of dyes present in the active composition may vary between 0.0% and 0.5%, preferably between 0.005% and 0.05%, the percentages being relative to the weight of the active composition.

The presence of a bittering agent may be desirable in order to render the product unpalatable, making it less likely for the active composition to be ingested, especially by young children. One can cite, as non-limiting examples, isopropyl alcohol, methyl ethyl ketone, methyl n-butyl ketone or yet a denatonium salt such as the denatonium benzoate known also under the trademark Bitrex™ (origin: Mac Farlan Smith Ltd.).

The bittering agent may be incorporated in the active composition in a total amount comprised between 0.0% and 5%, the percentages being relative to the total weight of the active composition. In the case of Bitrex™ the amount can be comprised between 0.0% and 0.1%, preferably between 10 and 500 ppm of the total weight of the active composition, whereas the other bittering agents above-mentioned are typically used in amounts from 0.5 to 5% by weight, when present.

The devices of the invention are preferably used in the form of air fresheners or deodorizers for rooms and cupboards, preferably open to daylight, and other closed environments such as cars for example. They may also assume the form of animal litter refreshers, linen perfuming articles and similar. They may be presented in the form of kits ready to be assembled by the user before activation thereof.

The following examples are further illustrative of the present invention embodiments, and further demonstrate the advantages of the invention devices relative to prior art teachings.

PREFERRED EMBODIMENTS OF THE INVENTION

In the examples, the following letters are used to designate the various parts or members of the device according to the invention:

(A) Casing or housing, or supporting frame
(B) Reservoir or bottle containing the volatile substance
(C) Coil or solenoid
(D) Volatile liquid substance
(F) Emitting or emanating member (in the form of a flag)
(G) Access gap or hole
(H) Housing holes or vents (I) Interface piece
(L) Moulded (plastic) component carrying a pivot and a lever piece
(M) Magnet
(P) Pivot
(PCB) Printed Circuit Board
(R) Retaining Clip
(S) Solar Cell
(W) Wick
(Z) Feet.

In general terms, for all configurations, the device is formed of the following parts and assembled in the following manner:

The reservoir or bottle (B) is filled with fragrance or formulation, the volatile liquid to be diffused (D). The latter may also be provided in a separate hermetic plastic pouch for example and be inserted inside the bottle upon assembly by the user.

For device transport, a foil barrier seal (E) (not shown) is hermetically fastened to the top of the bottle if the latter carries the volatile liquid.

The bottle is clipped or screwed into a moulded plastic component (L) which combines the features of a bottle cap, a lever extending from the cap, and pivot. Alternatively, this moulded plastic component (L) is packaged separately and can be clipped or screwed by the user onto the upper part of the reservoir upon assembling of the device by the user.

A porous component (F), the emanating member, possibly flat shaped and made of coloured die-cut paper or sintered plastic, is wrapped around, or joined to the top of a long rigid wick (W), for example by insertion in appropriately formed vertical grooves carved into the surface of the wick.

The rigid wick (W) is partly inserted into the top of the cap component (L) so as not to pierce the seal (E) (not shown), or is packaged separately and assembled by the user when the device is to be activated.

The whole assembly can then be lodged in a casing having a shape which allows this assembly to swing freely around the pivoting point.

The consumer may activate the device by pushing the wick through the seal (E) to the bottom of the bottle.

With reference to the figures presented hereafter, and according to the invention, the pivot (P) may be lodged in the cap of the reservoir and fixed to the casing, the assembly of reservoir, wick and emanating member being able to swing around the pivot bearing when manually activated or powered via a solar cell, for example.

In other embodiments, the pivot (P) is located above the whole assembly of reservoir, wick and emanating member, in a position fixed to the casing for example, and the whole assembly oscillates between two positions, around the pivoting point.

In both general arrangements the mass of the reservoir (B) acts as a pendulum to move the wick (W) and the emanating member (F) and therefore move air over the latter's diffusing surface to increase the rate of diffusion of the fragrance.

The swinging movement in both general arrangements can be caused manually, where the bottle (B) or optional lever part of the component (L) needs to be pushed to set the device going until the motion decays due to friction in the pivot bearing, air drag and movement of the fragrance in the bottle.

Alternatively, the device may be advantageously solar powered or battery powered. There is then provided a solenoid or coil (Cc or Cr) and a magnet (M), to drive the movement of the emanating member and of the full assembly. The solenoid and magnet are controlled by a printed circuit board (PCB) which may include capacitors or a battery, and be powered by a solar cell (S).

There are a number of ways to arrange the magnet and coil, solar panel and casing, leading to the alternatives shown in the figures described hereafter.

With reference to FIG. 1, the manually actuated device is completely enclosed by a casing (A1) provided with holes or vents (H) to allow air to move through. These holes (H) can be anywhere on the casing and in any quantity and shape. The wick (W) extends both up and down from the pivot (P) point and reaches close to the bottom of the inside of the reservoir (B). There is a flag (F) of sheet material that is an extension of the wick and which, together with upper part of the wick, extending outside the reservoir (B), forms the emanating member, fragrance evaporating from the surface of this component. The lever is part of a moulded piece (L) that also includes the pivot and cap for the bottle. Alternatively, the lever may have a textured surface or inscription to indicate interactivity.

Because the wick does not move in relation to the reservoir, a good seal can be maintained. The casing may have feet (Z) which are far enough apart to provide stability.

Figure 2A:
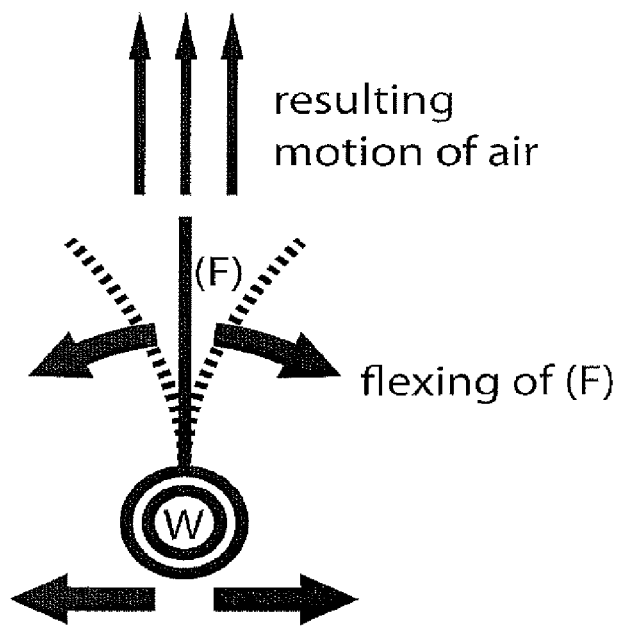
FIGS. 2a) and 2b) represent the swinging movement of the reservoir and wick/emanating structure and the air flow generated by bending of the emanating member flexible structure (FIG. 2a) or by rotation of the emanating member around the wick structure (FIG. 2b).
Figure 2B:
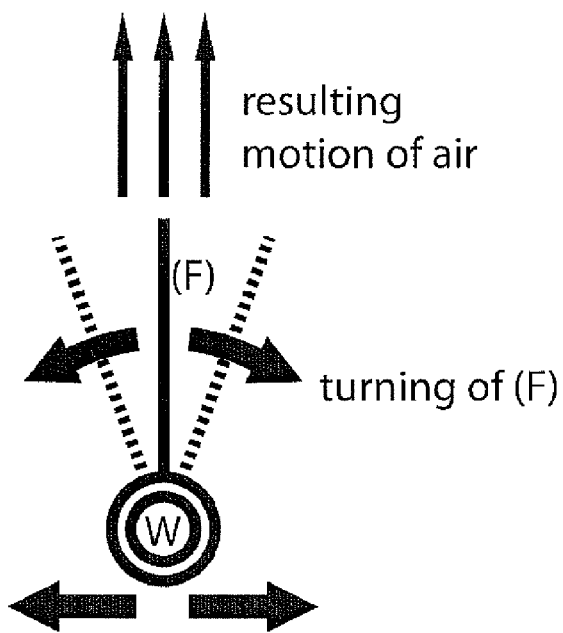

When the wick is swinging, the flag can either bend (see FIG. 2a and FIG. 14) or rotate (see FIG. 2b and FIG. 15) in relation to the axis of the wick. This will act as a fan moving air in one direction through the casing. In both cases there should be good conduction of the fragrance from the wick into the flag.

Figure 14:
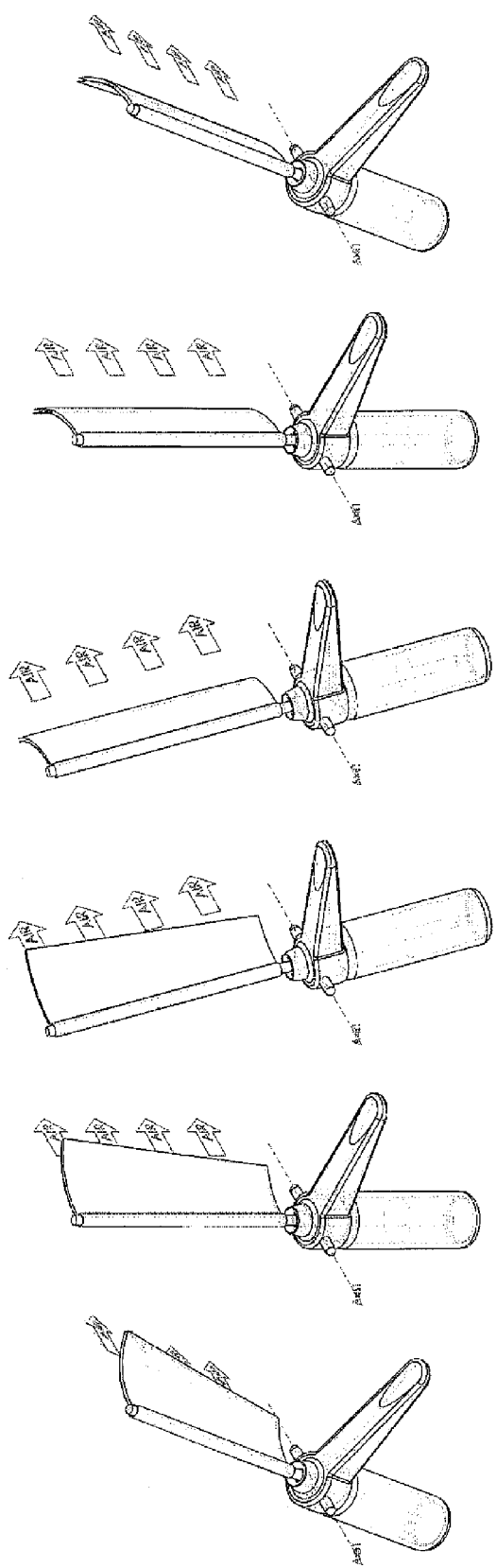
FIG. 14 is an animated view of the swinging movement of FIG. 2a).
Figure 15:
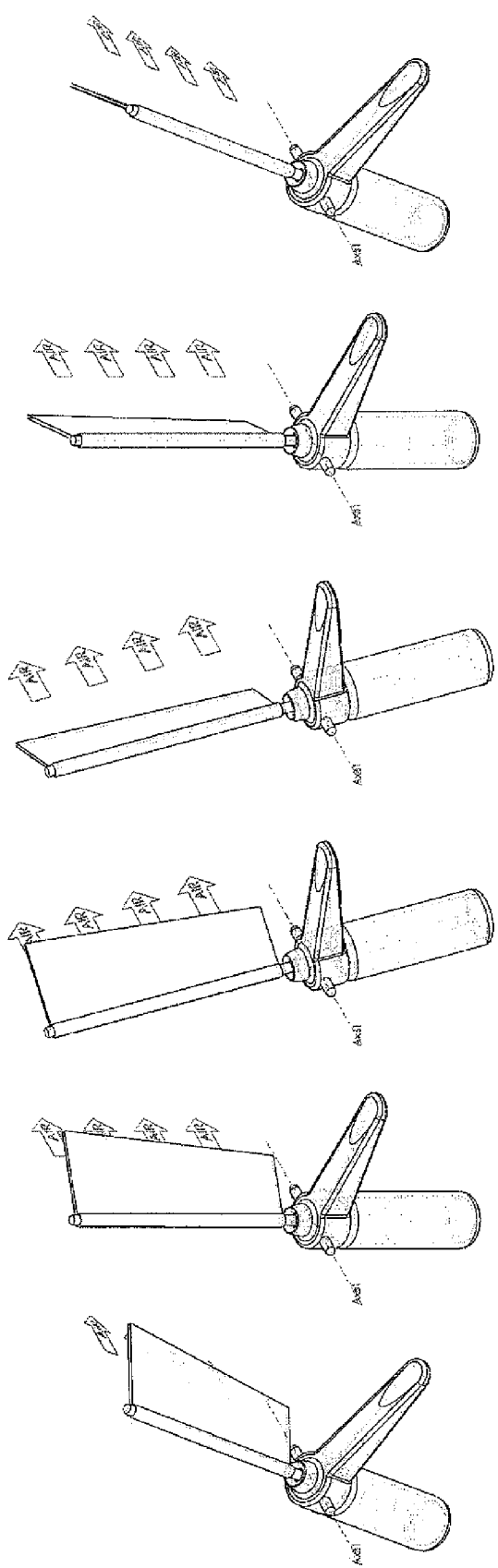
FIG. 15 is an animated view of the swinging movement according to FIG. 2b)

FIG. 14, respectively 15, show the various phases of the wick/emitting structure movement in the two cases, and how it generates the flux of air that drives the swinging movement of the air freshener around the pivot axis.

Figure 3A:
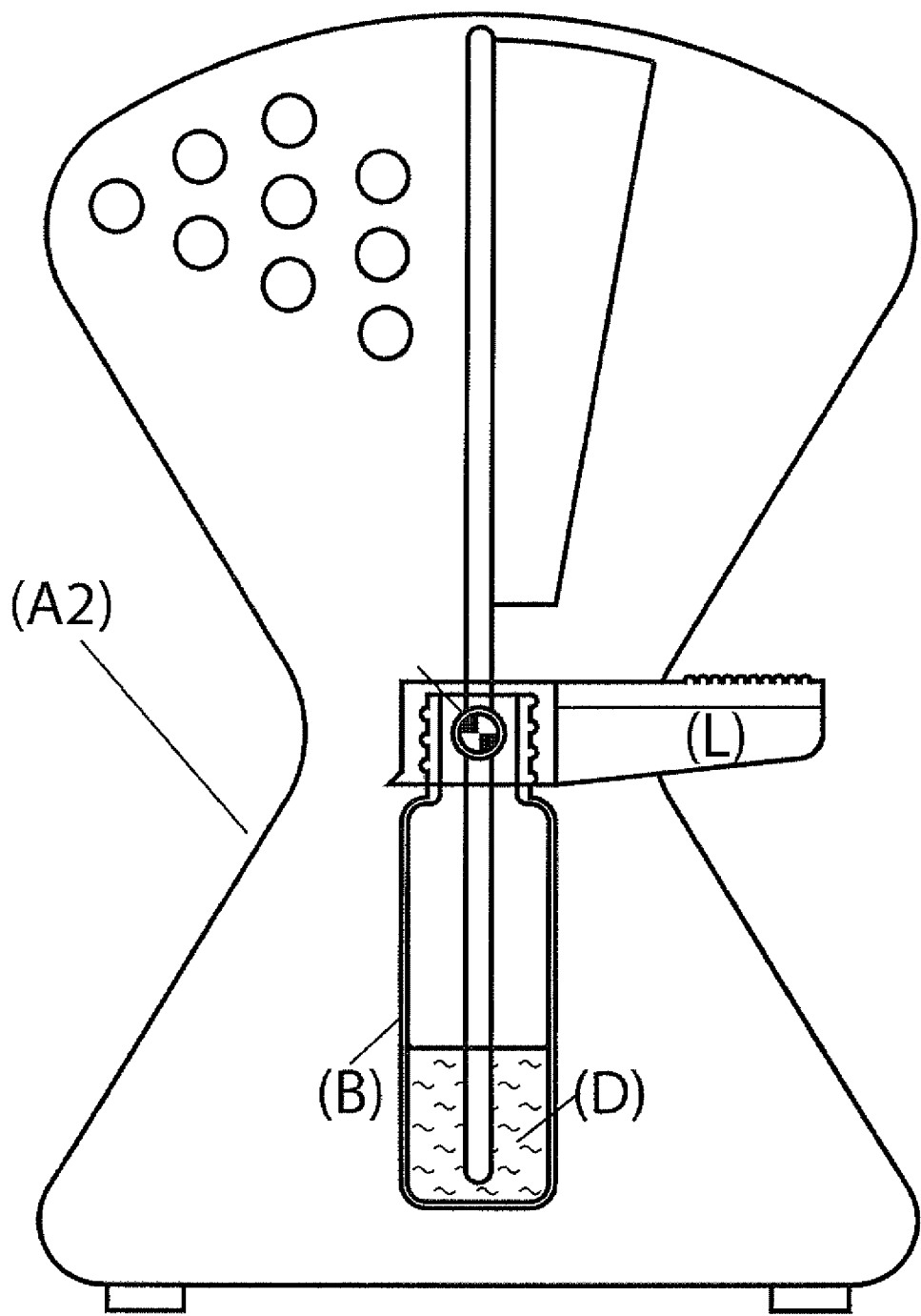
FIGS. 3 a) to 3 d) show elevated views, in cross section, of variants of the device of FIG. 1, wherein the device's casing or housing member A has a different shape to allow better access and actuation of the lever part of the moulded member L causing the movement or direct access to the bottle containing the active substance to allow displacement thereof.
Figure 3B:
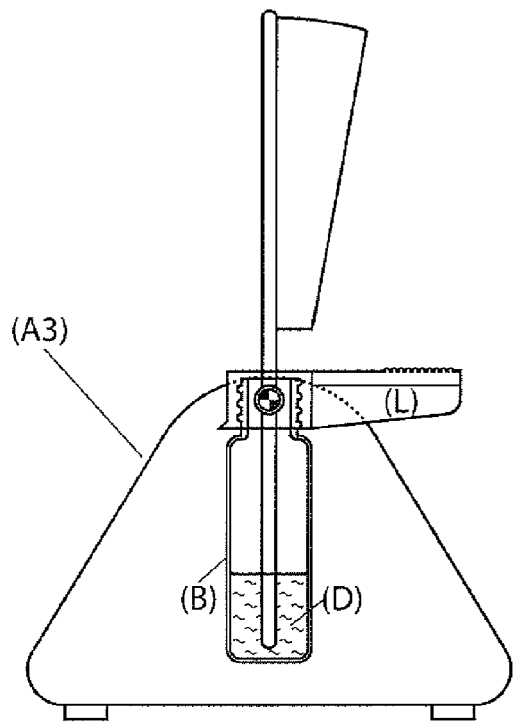
Figure 3C:
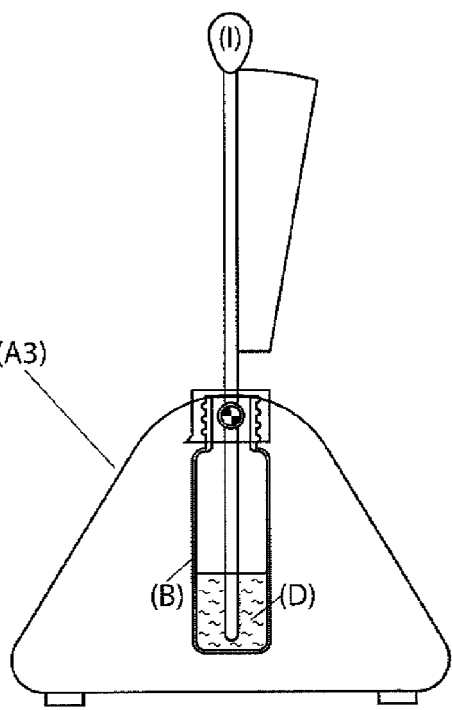
Figure 3D:
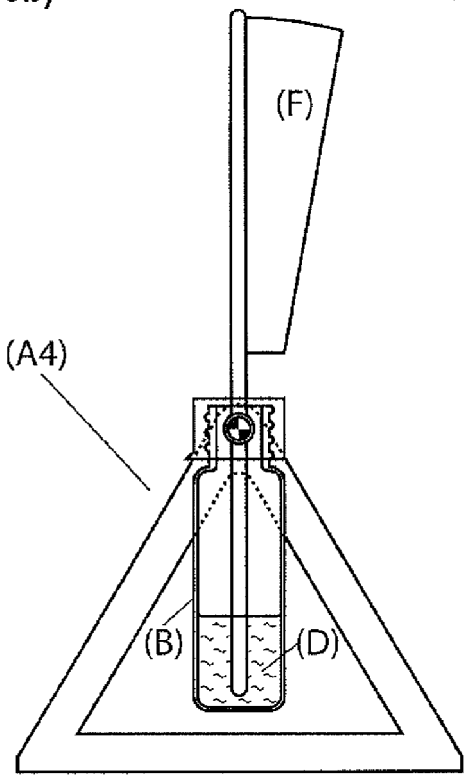

FIGS. 3a to 3d represent similar devices to that of FIG. 1, but wherein the casing has different shapes, allowing an easier access to the lever part of the piece (L) for activating the movement of the assembly. In the embodiment of FIG. 3a) the casing has a more curved shape in the middle, making it possible to activate the lever more easily. In FIG. 3b), the casing (A3) covers only the lower part of the device, leaving the moving upper part formed by wick and emitting member, visible. In FIG. 3c), there is provided at the top of the wick a handle part (I) as an alternative for getting the device swinging without directly touching any part of the emitting surface that may be wet with the fragrance (D). In FIG. 3d), the assembly comprising the reservoir (B) containing the volatile liquid (D), the wick and emitting member arrangement, and the cap comprising the pivot, is directly mounted through the latter on a frame (A4), instead of a casing, and the optional lever is not shown. The bottle (B) can be directly pushed through the frame, around the pivot (P) bearing, to start the motion.

Figure 4:
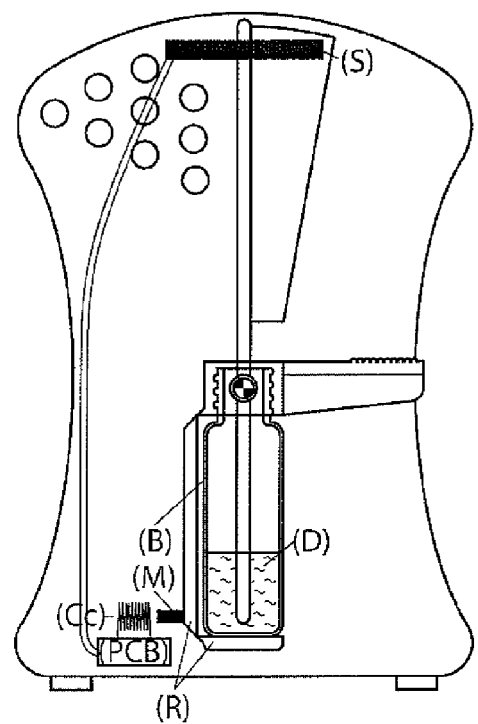
FIG. 4 is an elevated view, partially in cross section, of a solar panel powered device comprising a printed circuit board and a solenoid/magnet combination capable of triggering movement of the wick/emitting structure when a current passes through the printed circuit.

FIG. 4 represents a powered version of the device, comprising a solar cell (S) lodged in the casing in a position allowing it to be exposed to light. The solar cell is connected to a printed circuit which (PCB) feeding current to a solenoid or coil (Cc). A magnet (M) is arranged on the bottle, on an additional part (R) of the lever and pivot moulding which folds around the bottle to retain it, in a position allowing it to engage with the coil (Cc) upon current passage there-through, such that the magnet is attracted or repelled by the electromagnetic field generated by the current in the coil to drive the swinging motion. The folded piece (R) can be realized with plastic hinges.

The current may be created by a pulsed signal and the printed circuit (PCB) may be provided with components able to sense the position of the pendulum and alter the current accordingly.

In the configurations illustrated, the coil (C) and printed circuit board (PCB) are part of the casing assembly, and the magnet (M) is part of the swinging sub-assembly, but it goes without saying that the magnet can be lodged in a static manner and attached to the casing, the coil being then arranged on the swinging sub-assembly.

Figure 5:
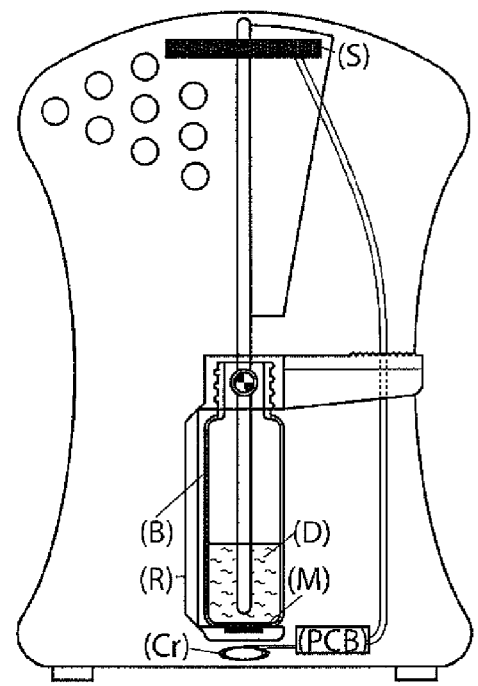
FIGS. 5 to 7 are elevated views, partially in cross section, of other variants of the solar panel powered device.

FIG. 5 represents a solar powered device similar to that of FIG. 4 but wherein the coil (Cr) is a flat radial solenoid, fixed on the inside bottom surface of the housing or casing, and the magnet (M) is retained inside the reservoir fold-around retainer piece (R).

Figure 6:
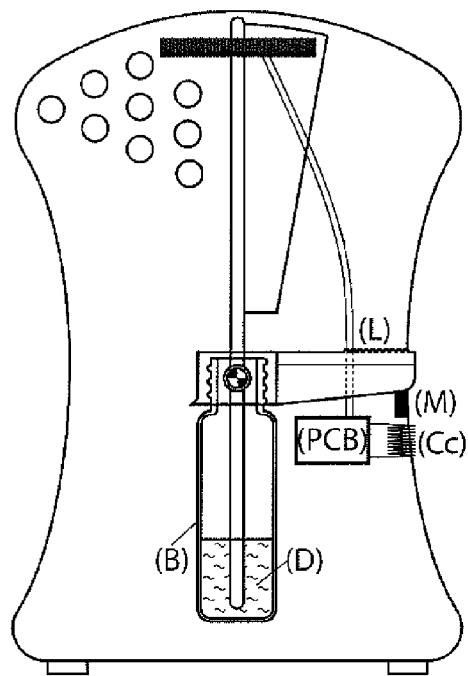

FIG. 6 shows yet another arrangement of a similar solar powered device, wherein a cylindrical coil (Cc) is mounted close to the lever part of the moulded piece (L), instead of close to the reservoir (B), the magnet (M) being attached to the lever.

Figure 7:
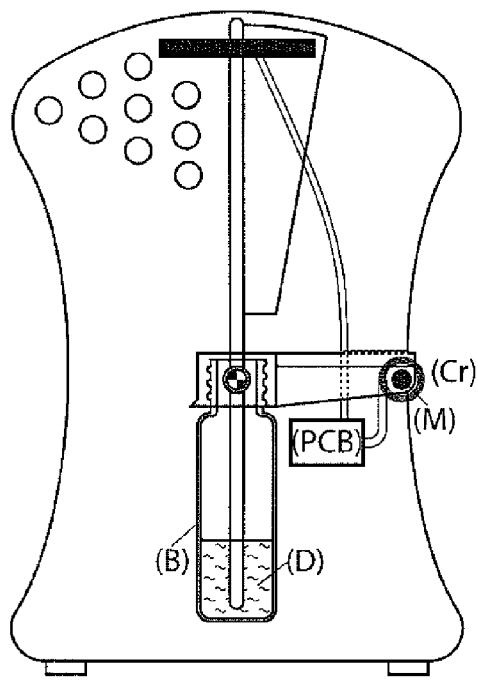

FIG. 7 illustrates yet another embodiment of the powered device according to the invention, wherein a flat radial coil (Cr) is mounted on the casing close to the lever and the magnet (M) is located on the lever in a position allowing it to be attracted to the solenoid upon passage of the electric current.

It is clear from the above that many variations of the arrangement of the coil, magnet and printed circuit parts can be used, the skilled person being able to choose the latter as a function of the shape and disposition of the air freshener components in the casing. Likewise, the position of the solar cell powering the printed circuit can be varied at will, and be fixed to the casing or to a component of the air freshener assembly of wick, reservoir and emanating member. The only essential condition is that it is positioned in a manner allowing it to be exposed to light.

In FIG. 8 for example, two other alternative positions of the solar cell are illustrated, FIG. 8a) showing an arrangement of the device wherein the solar cell or panel (S) is positioned on the front or back of the product, intended to face the light, whereas in FIG. 8b) the solar panel (S) is positioned on the side of the product's frame intended to face the light.

FIG. 9 illustrates other variants of a manually actionable device, wherein the pivot (P) is fixed at the top of the casing (A5 or A7), the wick (W), or its supporting shaft, hooking around the pivot. The bottle (B) is suspended below the wick (W). In FIG. 9a), the casing (A5) is provided with a gap or hole (G) on one of its faces, to allow external access to the reservoir (B) to set it swinging, as well as providing visibility of the amount of fragrance remaining. The casing may have feet (Z) spaced far enough apart to provide stability. As shown in FIG. 9b), the opening (G) may also be provided at the bottom of the casing (A7).

Figure 10:
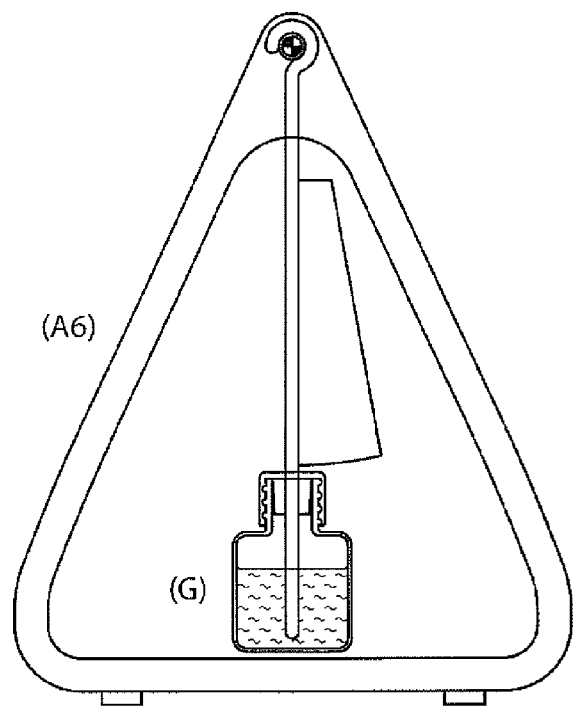
FIG. 10 is an elevated view of a device such as that of FIG. 9 but wherein the housing has been replaced by an open supporting frame.

This variant of the pivot fixation and position relative to the reservoir and its absorption/diffusion assembly is also adaptable to an open frame variant, as illustrated in FIG. 10, wherein the casing has been substituted for an open frame (A6) providing a large accessible opening (G) allowing full visibility of the device and access thereto to initiate its swinging movement around the pivot bearing.

In powered devices according to the invention, wherein the pivot is fixed in a position above the reservoir and diffusion member assembly, it is again possible to arrange the coil (C) and magnet (M) in a variety of ways.

Figure 11A:
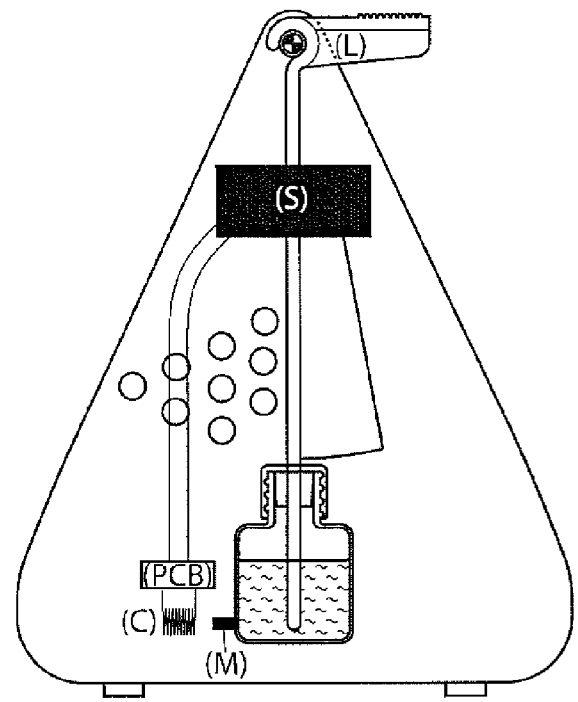
FIGS. 11 and 12 are elevated views partially in cross-section of powered devices according to the invention, similar to those of FIGS. 4 to 8, but wherein the pivot means are attached to the upper part of the housing or supporting frame of the device instead of being part of the moulded component also serving as the reservoir's cap.
Figure 11B:
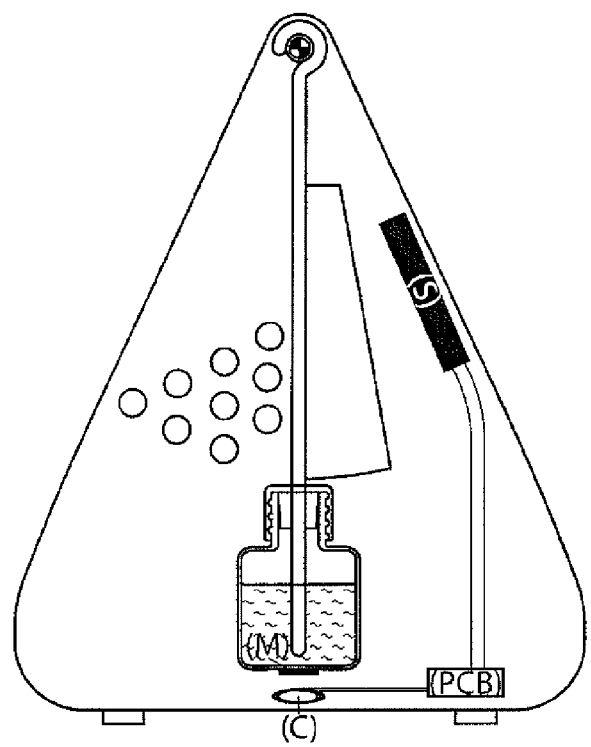

As illustrated in FIG. 11, a) and b), the magnet (M) is fixed on the reservoir, in a manner allowing it to enter a cylindrical or flat coil (C) at some point during the swinging movement and be attracted or repelled by the electromagnetic field generated by the current in the coil, to drive the motion.

Figure 12:
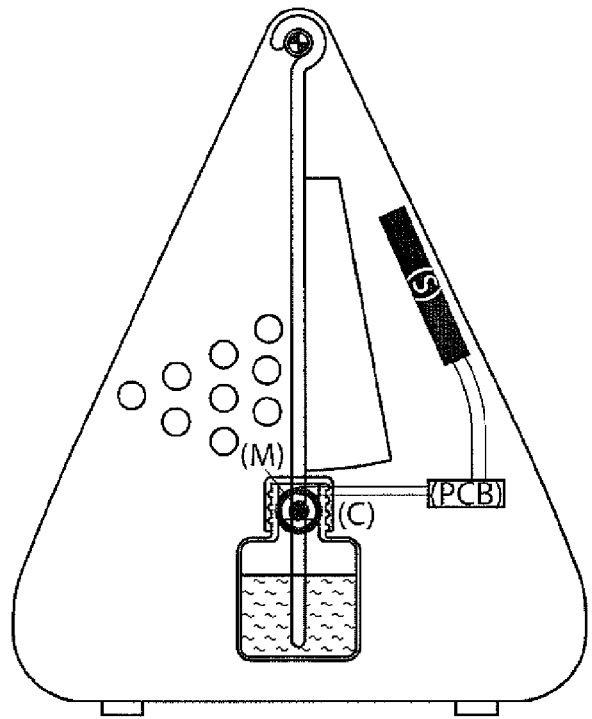

FIG. 12 shows an embodiment of the invention wherein the coil (C) is a flat radial solenoid fixed on the inside surface of the front or back of the casing, and the magnet (M) is incorporated into the cap of the reservoir.

Figure 13:
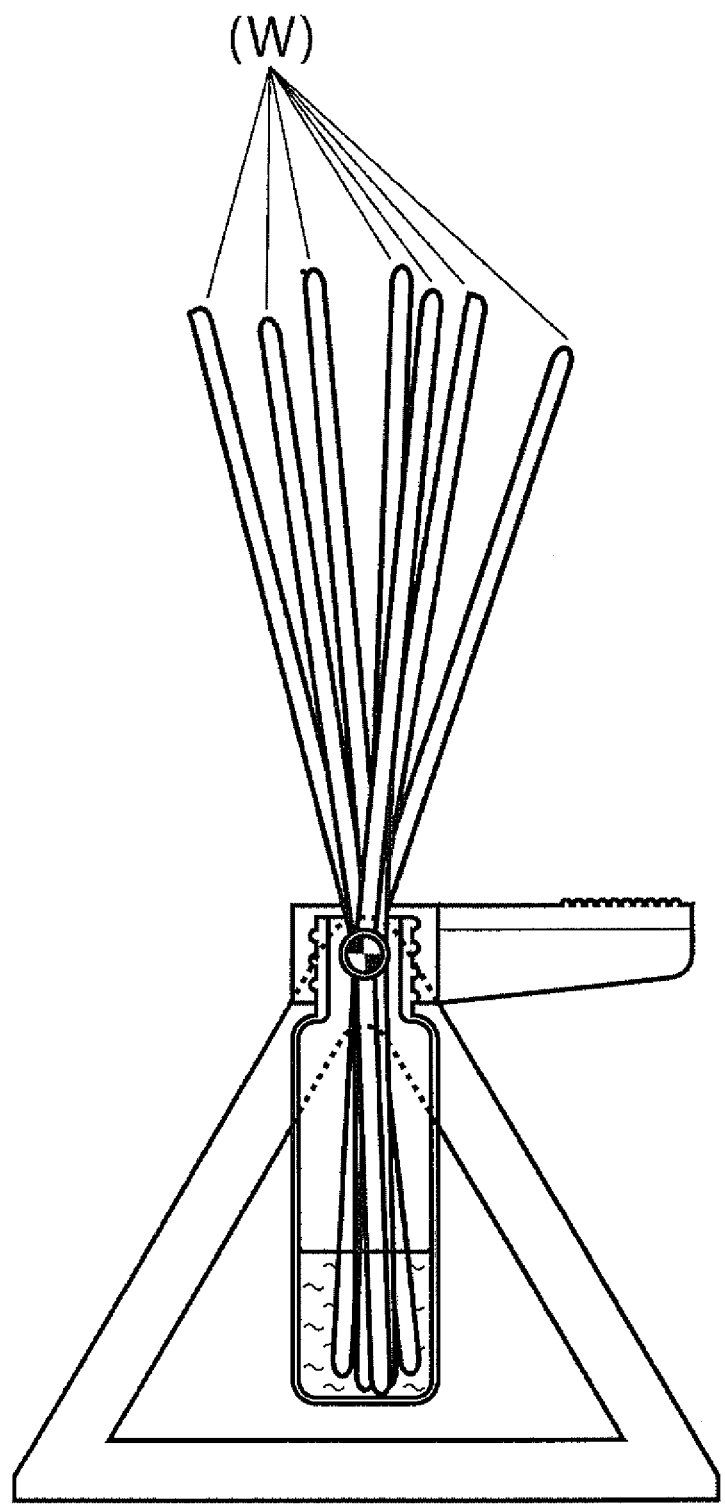
FIG. 13 is an elevated view of a device according to the invention which comprises a plurality of wick/emanating pieces.

FIG. 13 shows another embodiment of the invention with the same general features, except that a plurality of wick/emitting pieces (W) are provided through the upper aperture of the recipient containing the active substance. The pieces are in a reed like shape and they could also be disposed through a variety of smaller openings in the cap of the recipient, rather than the larger one shown, which accommodates all the reeds. This allows varying the aesthetic aspect of the air-freshener, as the reeds may be of different colours and be spaced out vertically, or in a conic bunch as the picture shows.

What is claimed is:

1. A device for dispensing an active liquid volatile substance into the surrounding atmosphere, said device comprising:
    a housing or a supporting frame,
    an assembly for providing forced ventilation of an evaporation surface impregnated with said active liquid volatile substance, the assembly comprising:
        a reservoir containing the active volatile substance and having an upper part that includes an opening;
        a cap lodged in the reservoir opening;
        at least one emanating member comprising said evaporation surface, the emanating member formed of a material capable of being impregnated with said active volatile substance and of allowing evaporation thereof into the device's surroundings; and
        at least one wick member formed of, or carrying, a porous material part capable of being impregnated with said active volatile substance, said wick member lodged through the cap into the reservoir opening so that a first portion of the wick member extends above the cap and a second portion of the wick member extends below the cap, wherein the wick member is in a position allowing it to be impregnated with the volatile substance, the second portion of the wick member does not move in relation to the reservoir, and the first portion of the wick member and the emanating member form a wick/emanating structure;
        a pivot directly connected to the cap that is lodged in the reservoir opening, wherein the assembly is arranged on the pivot so that the wick/emanating structure swings back and forth above the pivot and the second portion of the wick and the reservoir swings back and forth below the pivot, with the wick/emanating structure swinging back and forth for a period of time to cause forced ventilation of the evaporation surface of the emanating member;
    wherein the wick member is lodged in the device in a position allowing the second portion of the wick member to be in contact with the active volatile substance so that the active volatile substance can impregnate the wick member and the emanating member, and wherein the swinging movement of the wick/emanating structure, the reservoir and the second portion of the wick is triggered by manual, mechanical or electronically powered displacement.

2. The device according to claim 1, wherein the entire surface of the emanating member is impregnated with volatile substance and the maximum amount of the volatile substance absorbed in the wick and emanating members is less than about 20% by weight of the initial amount of volatile substance in the device.

3. The device according to claim 2, wherein the maximum amount of the volatile substance absorbed in the wick member and emanating member is between 5% and 15% by weight, and most preferably between 8% and 13% by weight, of the initial total weight of liquid contained in the device.

4. The device according to claim 1 wherein the wick member and emanating member are parts of a single piece forming the wick/emanating structure.

5. The device according to claim 1, comprising a plurality of wick/emanating structures.

6. The device according to claim 1, wherein the housing or supporting frame comprises holes or vents to allow diffusion of the active volatile into the device's surroundings upon its activation.

7. The device according to claim 6, comprising an activation means accessible from an exterior of the housing or frame to allow manual activation of the assembly's swinging movement.

8. The device according to claim 7, wherein the activation means consists of a lever which is part of a moulded component that also serves as the cap for the reservoir.

9. The device according to claim 8, wherein the pivot is lodged in said moulded component.

10. The device according to claim 9, wherein the device is solar powered with the housing or supporting frame carrying a solar panel and means for connecting said solar panel to a printed circuit board capable of generating an electric current on a solenoid arranged in a manner allowing the solenoid to engage a magnet to impart movement to the emanating member.

11. The device according to claim 1, wherein the active volatile substance is a liquid selected from the group consisting of a perfume, a deodorizing substance, an insecticide substance, an insect repellent or attracting substance, and an antibacterial or bacteriostatic agent.

12. The device according to claim 11, wherein the active volatile liquid is a non-aqueous perfume composition wherein at least 60% of the total weight of the non-aqueous perfume composition is formed of ingredients having a vapor pressure comprised between 4 Pa and 270 Pa.

13. The device according to claim 1, wherein the emanating member has a surface area comprised of one of between 50 $cm^2$ and 400 $cm^2$, and the surface area to the mass of liquid absorbed by the wick/emanating structure is a ratio between 20 $cm^2/g$ and 200 $cm^2/g$.

14. The device according to claim 13, wherein the emanating member has a surface area of between 75 $cm^2$ and 100 $cm^2$, and the surface area to the mass of liquid absorbed by the wick/emanating structure is a ratio between 30 $cm^2/g$ and 150 $cm^2/g$.

15. The device according to claim 14, wherein the emanating member has a surface area comprised between 100 $cm^2$ and 200 $cm^2$, and the surface area to the mass of liquid absorbed by the wick/emanating assembly a ratio between 40 $cm^2/g$ and 100 $cm^2/g$.

16. The device according to claim 1, wherein the emanating member is formed of filter paper having a thickness between 0.18 and 0.45 mm, or of sintered plastic having a thickness of 1.50 mm.

17. The device according to claim 1, wherein the device is a car freshener or deodorizer, a closet freshener, a mothproofer, an insecticide or an insect repellent device, or a combination thereof.

* * * * *